(12) United States Patent
Kim

(10) Patent No.: US 6,818,898 B2
(45) Date of Patent: Nov. 16, 2004

(54) X-RAY IMAGE SENSING DEVICE

(75) Inventor: Chang Won Kim, Seoul (KR)

(73) Assignee: LG. Philips LCD Co., Ltd., Seoul (KR)

( * ) Notice: Subject to any disclaimer, the term of this patent is extended or adjusted under 35 U.S.C. 154(b) by 0 days.

(21) Appl. No.: 10/207,063

(22) Filed: Jul. 30, 2002

(65) Prior Publication Data

US 2003/0057376 A1 Mar. 27, 2003

Related U.S. Application Data

(63) Continuation of application No. 09/534,439, filed on Mar. 24, 2000, now Pat. No. 6,492,643.

(30) Foreign Application Priority Data

Mar. 25, 1999 (KR) ..................... 1999-0010398

(51) Int. Cl.$^7$ .............................................. G01N 23/04
(52) U.S. Cl. ............................. 250/370.09; 250/370.14
(58) Field of Search ............................. 216/13, 14, 15; 250/580, 370.09, 370.01, 370.08, 370.14; 257/443, 444, 49; 438/738, 443, 737

(56) References Cited

U.S. PATENT DOCUMENTS 5,498,880 A  3/1996  Lee et al.
5,648,674 A  * 7/1997  Weisfield et al. ........... 257/428

* cited by examiner

Primary Examiner—Constantine Hannaher
Assistant Examiner—Timothy J. Moran
(74) Attorney, Agent, or Firm—McKenna Long & Aldridge LLP

(57) ABSTRACT

An X-ray image sensing device is manufactured to prevent an open of a ground line. The X-ray image sensing device has a plurality of pixels in a matrix configuration. A pixel includes: a photoelectric conversion part to receive X-rays and generate electric charges; a charge storage part to accumulate the electric charges produced in the photoelectric conversion part, having a capacitor electrode, a pixel electrode and a dielectric layer located between the pixel electrode and the capacitor electrode, a ground line for discharging residual charges in the charge storage part, positioned on the capacitor electrode to electrically contact the capacitor electrode, and extending to the adjacent pixel; and a switching part to control release of the charges stored in the charge storage part. In one case, the capacitor electrode extends to an adjacent pixel. Alternatively, the capacitor electrode has an end contact line, contacting the ground line, with a length greater than the width of the ground line.

12 Claims, 7 Drawing Sheets

X-RAY IMAGE SENSING DEVICE

This application is a continuation application of Ser. No. 09/534,439 filed on Mar. 24, 2000, now U.S. Pat No. 6,492,643 which is hereby incorporated by reference as if fully set forth herein.

CROSS REFERENCES TO RELATED APPLICATIONS

This application claims the benefit of Korean Patent Application No. 1999-10398, filed on Mar. 25, 1999, which is hereby incorporated by reference for all purposes as if fully set forth herein.

BACKGROUND OF THE INVENTION

1. Field of the Invention

The present invention relates to an X-ray image sensing device, and more particularly to an X-ray image sensing device fabricated utilizing a Thin Film Transistor (TFT) array process.

2. Description of Related Art

An X-ray detection method for medical diagnosis which has been widely used is such that an X-ray detecting film is used to produce a photograph and some predetermined printing procedure is required to obtain the result.

However, digital X-ray sensing devices (referred to hereinafter as X-ray sensing devices) employing a TFT have been developed recently due to the development of semiconductor technology. This X-ray sensing device has an advantage that a real time diagnosis can be obtained immediately after photographing because it uses a TFT as a switching element.

FIG. 1 is a schematic cross-sectional view illustrating the structure and operation of an X-ray image sensing device 100 which comprises a lower substrate 1, a thin film transistor 3, a storage capacitor 10, a pixel electrode 12, a photoconductive film 2, a protection film 20, a conductive electrode 24 and a high voltage direct current (DC) power supply 26.

Photoconductive film 2 produces internal electric signals, i.e. electron-hole pairs in proportion to the strength of external signals, such as incident electromagnetic waves or magnetic waves. That is, the photoconductive film 2 serves as a converter to detect external signals, particularly X-rays, and convert them into electric signals. Either the electrons or holes are gathered at pixel electrode 12 located beneath the photoconductive film 2, depending on a voltage ($E_v$) applied to the conductive electrode 24 by the high voltage DC power supply 26, and then are stored in storage capacitor 10 formed in connection with a ground line grounded externally. Charges stored in the storage capacitor 10 are transferred to the TFT 3, controlled externally, to an external image display device to form X-ray images.

In an X-ray image sensing device, to detect and convert even the weakest X-ray signal into an electric charge, it is required to decrease the trap state density for the electric charge in the photoconductive film 2 and to decrease the amount of current in non-vertical directions by applying a relatively high voltage (more than $10V/\mu m$) in the vertical direction between the conductive electrode 24 and the pixel electrode 12.

FIG. 2 is a cross-sectional view schematically illustrating a conventional X-ray image sensing device. U.S. Pat. No. 5,498,880 discloses an example of this kind of structure, wherein the pixel electrode 12 extends over the upper part of TFT 3 to prevent the trapping of electric charges at the upper part of TFT 3, induced from the electric charges produced in photoconductive film 2 by X-ray energy.

A capacitor electrode 40 made of transparent conducting material is formed on the gate insulating layer 34a on the substrate 1. A dielectric layer 34b is formed on the capacitor electrode 40 and patterned to form the ground line 42, which should extend to the adjacent pixel. The ground line 42 is formed on the exposed portion of the capacitor electrode 40. A protection layer 46 is formed on the TFT 3 to protect it from external impacts or humidity. A pixel electrode 12 is formed on the protection layer 46 contacting the dielectric layer 60 through a contact hole formed in the dielectric layer 34b. The pixel electrode 12 and the capacitor electrode 40 are the two electrodes of the storage capacitor.

The ground line 42 contacting the capacitor electrode 40 discharges the residual charges remaining in the storage capacitor.

FIG. 3a is a plan view illustrating a section of the conventional X-ray sensing device and shows a gate line 50 disposed crosswise and a data line 52 disposed lengthwise. A TFT 3 is formed as a switching element in the region where the gate line 50 and data line 52 cross and a ground line 42 is disposed parallel to the data line 52. The ground line 42 and the dielectric layers 34b are positioned on the capacitor electrode 40. The pixel electrode 12 covers the ground line 42 and the dielectric layers 34 to form the storage capacitor. The ground line 42 extends to the adjacent pixel (not shown) and contacts the capacitor electrode of the adjacent pixel.

FIG. 3b is an enlarged view of portion A of FIG. 3a, showing an electrical line short that often occurs in the conventional X-ray image sensing device. In the figure, line short portions A' are seen in the ground line 42 at the boundary with the capacitor electrode 40. This occurs because a metal used for the ground line 42 is not adhered well on the capacitor electrode 40 made of transparent conducting material and the etching solution invades from both ends to inside the step difference region during the wet etching of the ground line 42.

The defect can be seen more clearly in FIG. 3c that is a cross-sectional view taken along the line III—III of FIG. 3b, showing the A' part where the ground line 42 has an open portion in the step difference region of the capacitor electrode 40 and ground line 42.

The open in the ground line may cause the problem that the residual charges can not be removed efficiently, which deteriorates the quality of X-ray images.

SUMMARY OF THE INVENTION

This invention has been developed in order to address the above-described problem.

An object of this invention is to provide an X-ray image sensing device wherein the ground line open is not caused.

Another object of this invention is to provide an X-ray image sensing device having a ground line with reduced resistance.

In order to accomplish the above objects, this invention provides in one aspect, an X-ray image sensing device having a plurality of pixels in a matrix configuration, a pixel including a photoelectric conversion part to receive X-rays and generate electric charges from the X-rays; a charge storage part to accumulate the electric charges produced in the photoelectric conversion part, having a capacitor electrode, a pixel electrode and a dielectric layer located between the pixel electrode and the capacitor electrode, which extends to an adjacent pixel; a ground line for discharging residual charges in the charge storage part, positioned on the capacitor electrode to electrically contact the capacitor electrode, and extending to the adjacent pixel; and a switching part to control release of the charges stored in the charge storage part.

This invention also provides in another aspect, an X-ray image sensing device having a plurality of pixels in a matrix configuration, a pixel including a photoelectric conversion part to receive X-rays and generate electric charges from the X-rays; a charge storage part to accumulate the electric charges produced in the photoelectric conversion part, having a capacitor electrode, a pixel electrode and a dielectric layer located between the pixel electrode and the capacitor electrode; a ground line for discharging residual charges in the charge storage part, positioned on the capacitor electrode to electrically contact the capacitor electrode, and extending to an adjacent pixel; and a switching part to control release of the charges stored in the charge storage part, wherein the capacitor electrode is shaped so that an end contact line of the capacitor electrode with the ground has a length greater than a width of the ground line.

Preferably, the photoelectric conversion part is comprised of a photoconductive film and conductive electrode.

Preferably, the conductive film is preferably manufactured of a material selected from the group consisting of amorphous selenium, $HgI_2$, PbO, CdSe, thallium bromide and cadmium sulfide.

Preferably, the ground line is preferably made of Chrome.

Preferably, the capacitor electrode is preferably made of transparent conducting material.

BRIEF DESCRIPTION OF THE DRAWINGS

For a more complete understanding of the present invention and the advantages thereof, reference is now made to the following descriptions taken in conjunction with the accompanying drawings, in which like reference numerals denote like parts, and in which:

FIG. 3b is an enlarged view of a portion A of FIG. 3a;

DETAILED DESCRIPTION OF PREFERRED EMBODIMENTS

An X-ray image sensing device of this invention comprises, in general, N first signal lines in a first direction and M second signal lines in a second direction substantially crossing each other to form M×N matrix-type pixels.

The pixel comprises a photoelectric conversion part to receive X-rays and generate electric charges depending on the received amount of X-ray energy; a charge storage part to accumulate the electric charges produced in the photoelectric conversion part, which has a capacitor electrode, a pixel electrode and a dielectric layer located between the pixel electrode and the capacitor electrode; a ground line electrically contacting the capacitor electrode; and a switching part to control the release of the charges stored in the charge storage part.

The first and second embodiments are directed toward improving the boundary between the capacitor electrode and the ground line. A first embodiment removes a step difference portion between the capacitor electrode and the ground line. A second embodiment forms a concave line in the capacitor electrode at the boundary.

The photoelectric conversion part above mentioned comprises a photoconductive film and a conductive electrode.

The photoconductive film is desirably manufactured of a material selected from the group consisting of amorphous selenium, $HgI_2$, PbO, CdSe, thallium bromide and cadmium sulfide.

Figure 1:
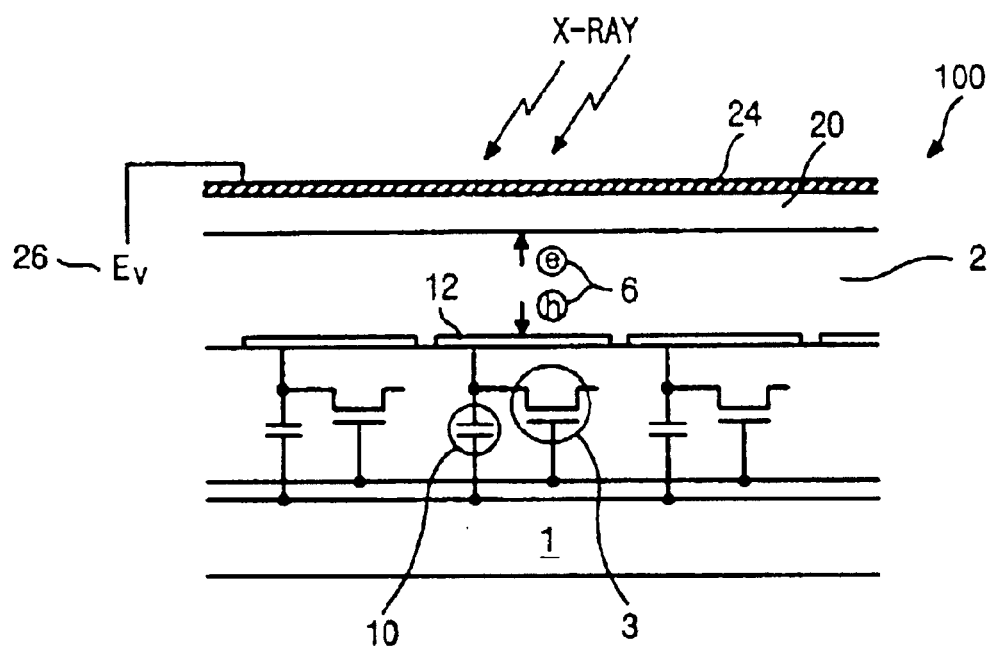
FIG. 1 is a cross-sectional view of an enlarged scale illustrating the principle of an X-ray image sensing device.
Figure 2:
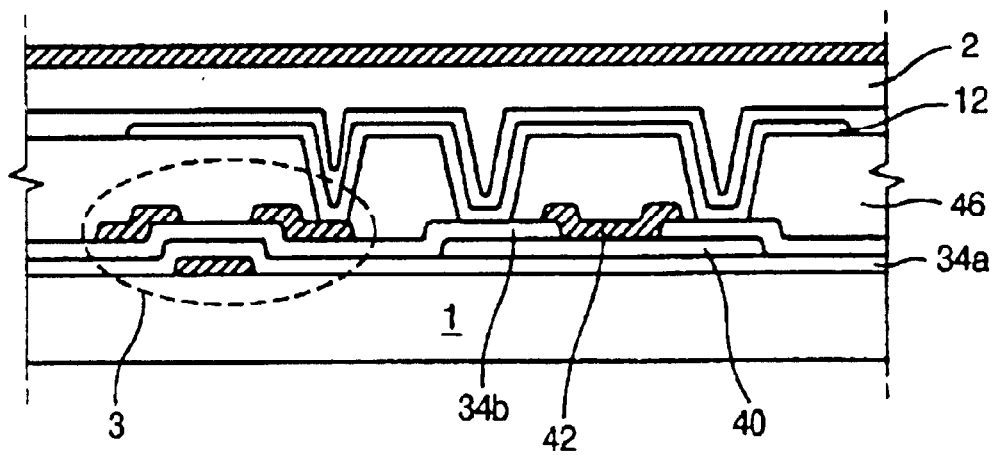
FIG. 2 is a cross-sectional view of an enlarged scale illustrating one pixel of an X-ray image sensing device.
Figure 3A:
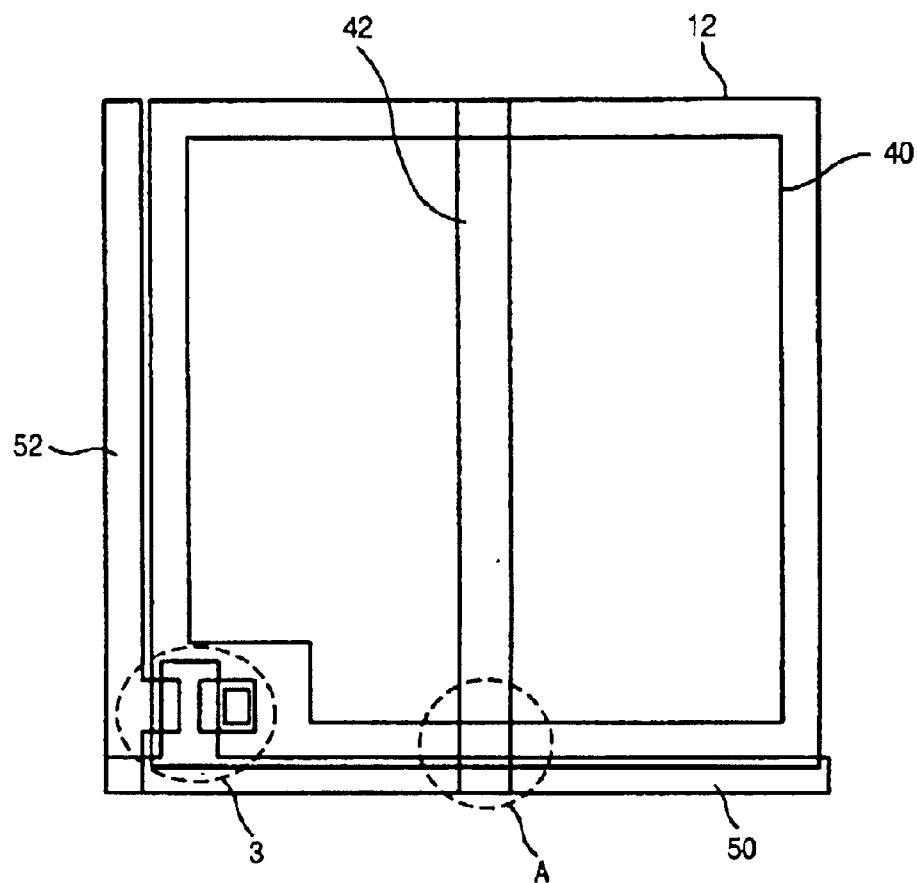
FIG. 3a is a plan view of an enlarged scale illustrating one pixel of the conventional X-ray image sensing device.
Figure 3B:
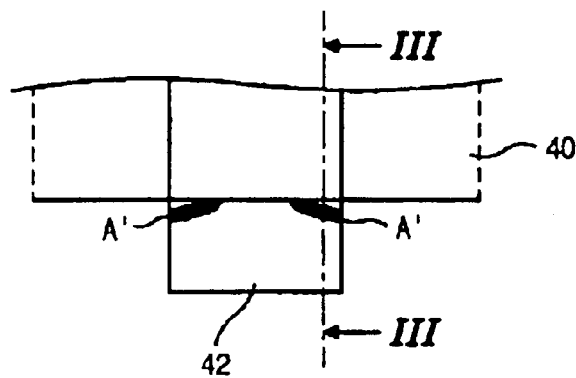
Figure 3C:
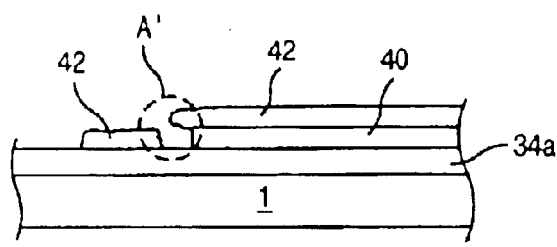
FIG. 3c is a cross-sectional view taken along the line III—III of FIG. 3b.
Figure 4:
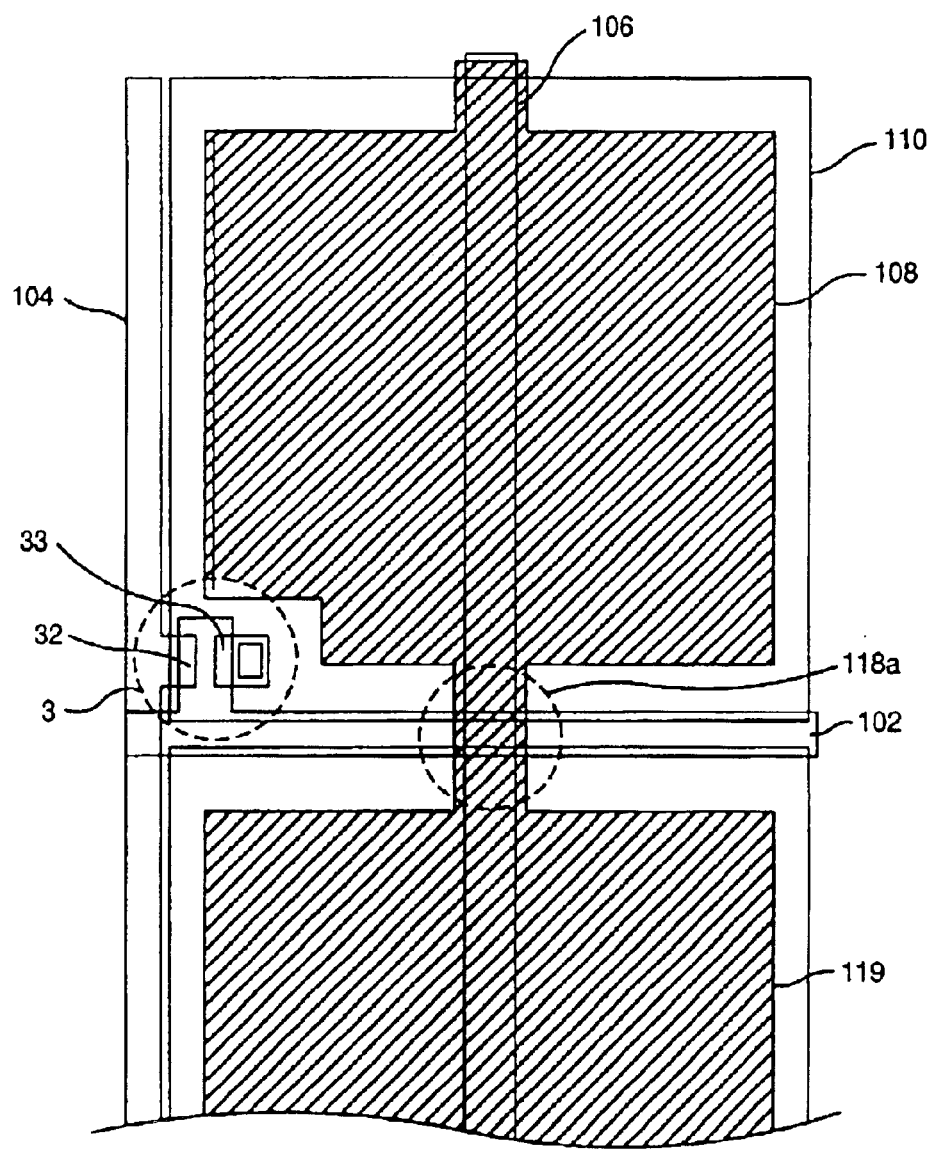
FIG. 4 is a plan view of an enlarged scale illustrating part of an X-ray image sensing device manufactured in accordance with one embodiment of the invention.

FIG. 4 is a plan view of one pixel of an X-ray image sensing device panel according to the first embodiment. The figure shows a gate line 102 disposed crosswise and a drain line 104 disposed lengthwise, together with a TFT 3 as a switching element formed in the region where the gate line 102 and drain line 104 cross. A ground line 106 is located in the central region as a common electrode grounded in common with another ground line (not shown) of the adjacent pixels.

A capacitor electrode 108 and a pixel electrode 110 are formed to constitute a storage capacitor (S), and a silicon nitride film is formed between the capacitor electrode 108 and the pixel electrode 110 as a dielectric.

The capacitor electrode 108 extends to the adjacent pixel and is connected to the adjacent capacitor electrode 119. The ground line 106 is formed on the capacitor electrode 108, and extends to the adjacent pixel. The connection portion 118a of the capacitor electrode 108 has a width larger than that of the ground line 106. Thus, there is no step difference portion of the capacitor electrode 108 beneath the ground line 106. Therefore, an open of the ground line 106 that may occur during the etching process for the ground line 106 does not occur. And according to this embodiment of the invention, even if an open of the ground line 106 occurs, since the capacitor electrode extends to the adjacent pixel, there cannot occur any error in operation of the X-ray image sensing device. Besides the prevention of an open in the ground line, since the ground line 106 extends contacting with the capacitor electrode, the resistance of the ground line is reduced.

Figure 5:
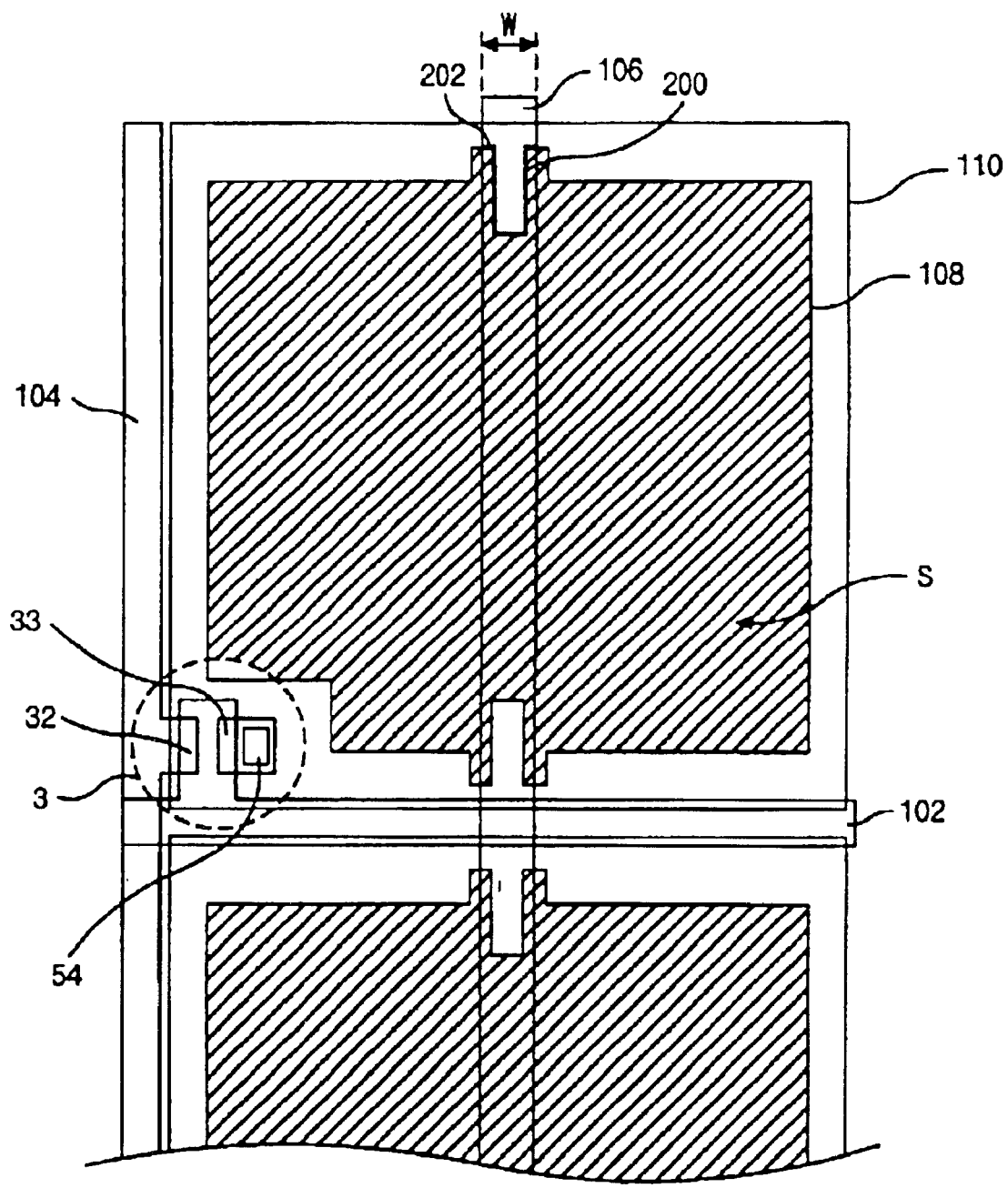
FIG. 5 is a plan view of an enlarged scale illustrating part of an X-ray image sensing device manufactured in accordance with a second embodiment of the invention.

Referring to FIG. 5, a second embodiment will be described. In this embodiment, the ground line 106 extends in one direction and contacts the capacitor electrode as in the first embodiment, but configuration of the capacitor electrode 108 is changed. The step difference portion of the capacitor electrode 108 beneath the ground line 106 is designated as the contact line 200. The contact line 200 is preferably concave-shaped, and the length of the contact line 200 is longer than the width "w" of the ground line 106. And the step difference portion line 200 of the capacitor electrode 108 has an end contact line 202 that contacts the ground line 106 at the end of the capacitor electrode 108 in the extending direction of the ground line 106 and the end contact line 202 is shorter than the width of the ground line 106. The end contact line 202 of the capacitor electrode 108 is a passage that etchant may penetrate, but it is much shorter than the width "w" of the ground line 106. Thus, while etching the ground line material, which is usually Chrome (Cr), the etchant can not penetrate the whole width "w" of the ground line 106. Thus, the open of the ground line 106 is prevented while forming the ground line 106 with etchant.

Figure 6:
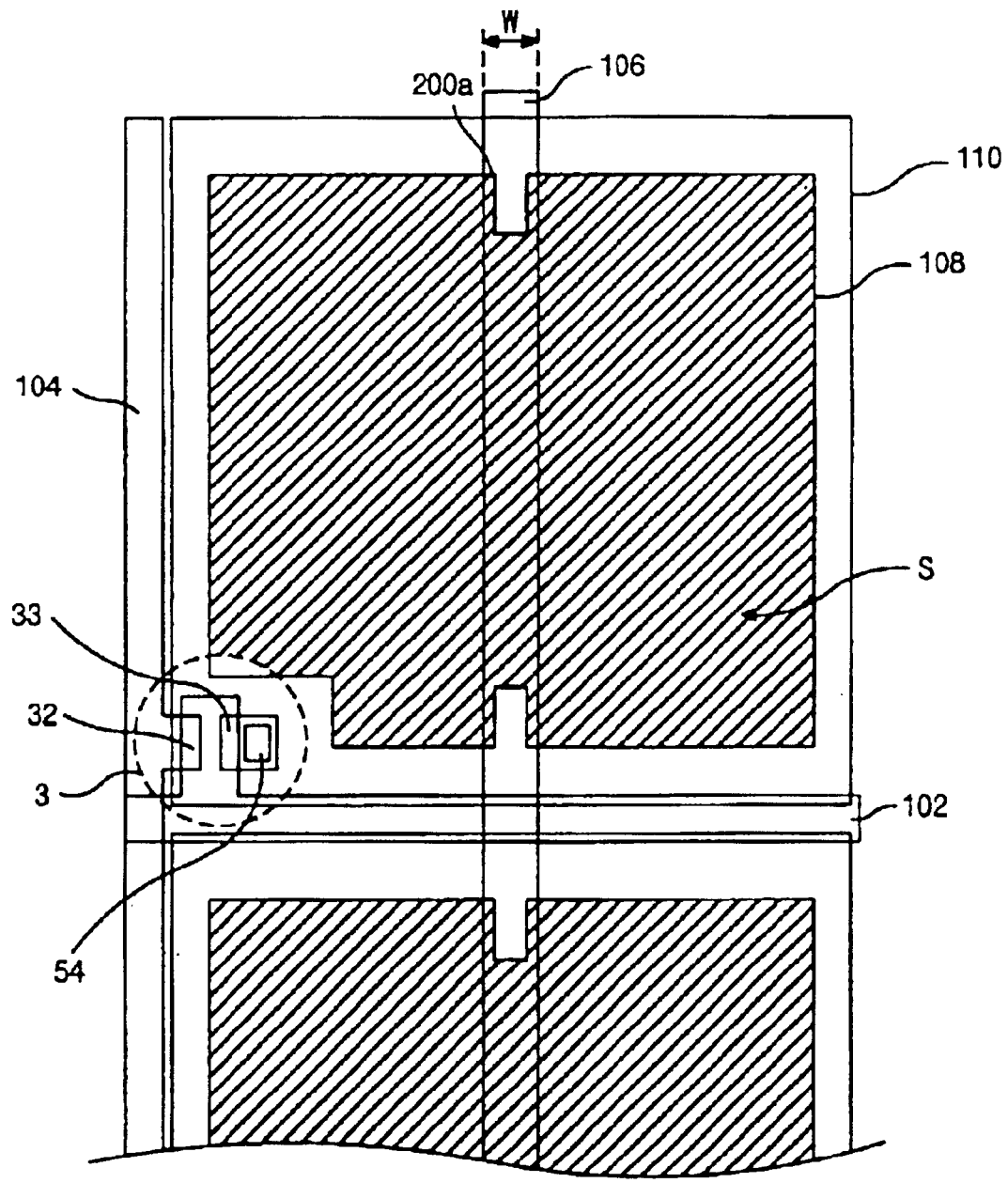
FIGS. 6 to 8 are plan views of an enlarged scale illustrating modified examples of an X-ray image sensing device manufactured according to the second embodiment.
Figure 7:
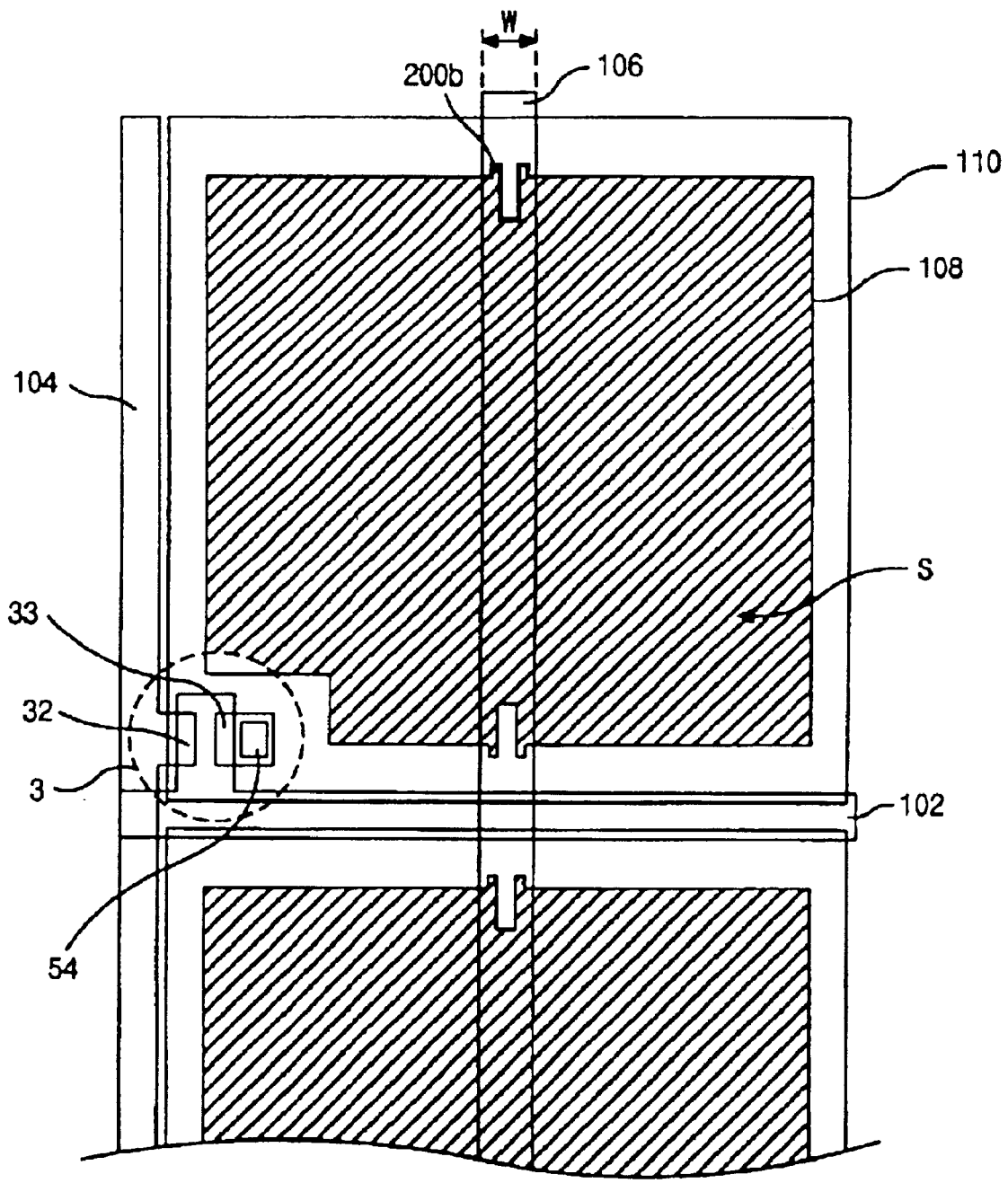
Figure 8:
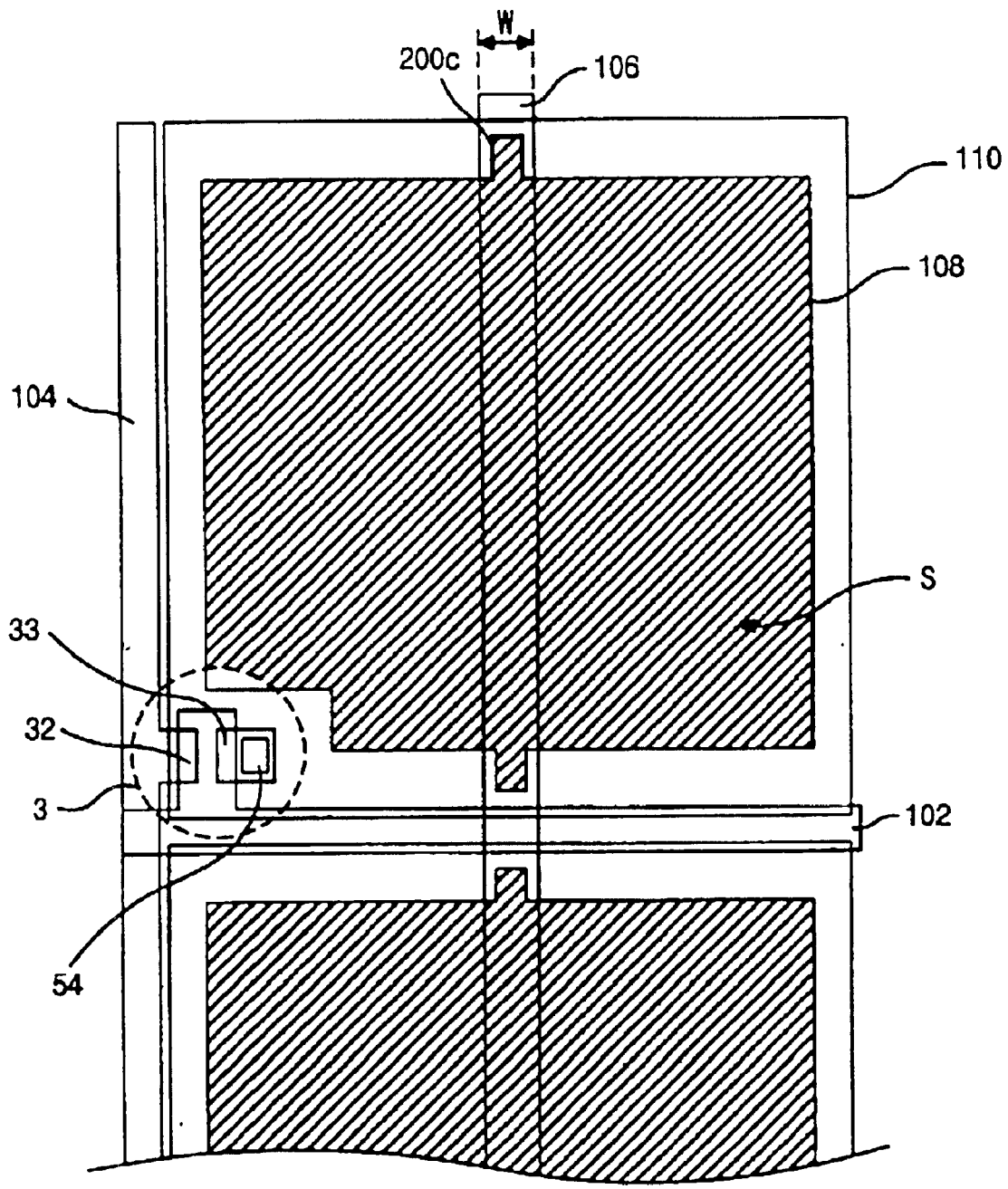

FIGS. 6 to 8 show modified examples of the second embodiment. The step difference portion of the capacitor electrode 108 beneath the ground line 106, that is, each of the contact lines 200a, 200b and 200c of FIGS. 6 to 8, respectively are longer than the width "w" of the ground line 106, which means that a passage for the etchant becomes long, leading to a reduction of the possibility of an open of the ground line 106.

Other embodiments and features of the invention will be apparent to the skilled in the art from consideration of the specification and practice of the invention disclosed herein. It is intended that the specification and examples be considered as exemplary only, with the true scope and spirit of the invention being indicated by the following claims.

What is claimed is:

1. An X-ray image sensing device having a plurality of pixels in a matrix configuration, a pixel comprising:
   a photoelectric conversion part to receive X-rays and generate electric charges from the X-rays;
   a charge storage part to accumulate the electric charges produced in the photoelectric conversion part, having a capacitor electrode, a pixel electrode and a dielectric layer located between the pixel electrode and the capacitor electrode, wherein the capacitor electrode extends to an adjacent pixel;
   a ground line for discharging residual charges in the charge storage part, positioned on the capacitor electrode to electrically contact the capacitor electrode, and extending to the adjacent pixel; and
   a switching part to control release of the charges stored in the charge storage part.

2. The X-ray image sensing device of claim 1, wherein the photoelectric conversion part comprises a photoconductive film and a conductive electrode.

3. The X-ray image sensing device of claim 2, wherein the photoconductive film is manufactured of a material selected from a group consisting of amorphous selenium, $HgI_2$, PhO, CdSe, thallium bromide and cadmium sulfide.

4. The X-ray image sensing device of claim 1, wherein the ground line is made of Chrome.

5. The X-ray image sensing device of claim 1, wherein the capacitor electrode is made of transparent conducting material.

6. The X-ray image sensing device of claim 1, wherein the switching part is a TFT.

7. An X-ray image sensing device comprised of at least two pixels, the device, comprising:
   a photoelectric conversion part for converting X-rays into electric charges;
   a capacitor in each pixel for accumulating the electric charges, said capacitors each including a transparent capacitor electrode, a pixel electrode, and a dielectric disposed between the pixel electrode and the capacitor electrode, wherein the capacitor electrode of one capacitor extends to be connected with the capacitor electrode of the other capacitor;
   a ground line that extends along and electrically contacts each capacitor electrode, wherein the ground line is disposed between the capacitor electrode and the pixel electrode; and
   a switch for each capacitor, wherein each switch selectively controls the discharge of its associated capacitor.

8. The X-ray image sensing device of claim 7, wherein the photoelectric conversion part includes a photoconductive film and a conductive electrode.

9. The X-ray image sensing device of claim 8, wherein the photoconductive film includes a material selected from a group consisting of amorphous selenium, $HgI_2$, PbO, CdSe, thallium bromide, and cadmium sulfide.

10. The X-ray image sensing device of claim 7, wherein the ground line is made of Chrome.

11. The X-ray image sensing device of claim 7, wherein the pixel electrode is made of a transparent conducting material.

12. The X-ray image sensing device of claim 7, wherein the switch is a TFT.

* * * * *